United States Patent

Mumolo et al.

[11] Patent Number: 5,366,373
[45] Date of Patent: Nov. 22, 1994

[54] DENTAL ARTICULATOR

[76] Inventors: Frank Mumolo, 1042 Benmore Ave., Franklin Square, N.Y. 11010; Helmut W. Pufal, 58-44 78th Ave., Glendale, N.Y. 11385

[21] Appl. No.: 164,559
[22] Filed: Dec. 10, 1993
[51] Int. Cl.$^5$ ............................................. A61C 11/00
[52] U.S. Cl. ................................... 433/58; 433/63
[58] Field of Search ................ 433/54, 57, 58, 61, 433/62, 63, 64, 65, 213

[56] References Cited

U.S. PATENT DOCUMENTS

| | | | |
|---|---|---|---|
| 2,688,800 | 9/1954 | Gerber | 433/58 |
| 4,175,325 | 11/1979 | Beckwith | 433/58 |
| 4,721,463 | 1/1988 | Lee | 433/54 |
| 4,764,113 | 8/1988 | Hiranuma | 433/58 |
| 4,797,097 | 1/1989 | Cohn | 433/54 |

Primary Examiner—Cary E. O'Connor

[57] ABSTRACT

The dental articulator to test the "bite" of cast upper and lower jaw dentures in which a rearward horizontally oriented pivot of the upper jaw denture is mounted for pivotal traverses in an open arcuate-shaped cooperating support of the lower jaw denture and this simple articulating construction and vertical adjustment between the two dentures is due to a large extent to the use of rubber bands to hold the referenced pivots on their arcuate supports.

3 Claims, 2 Drawing Sheets

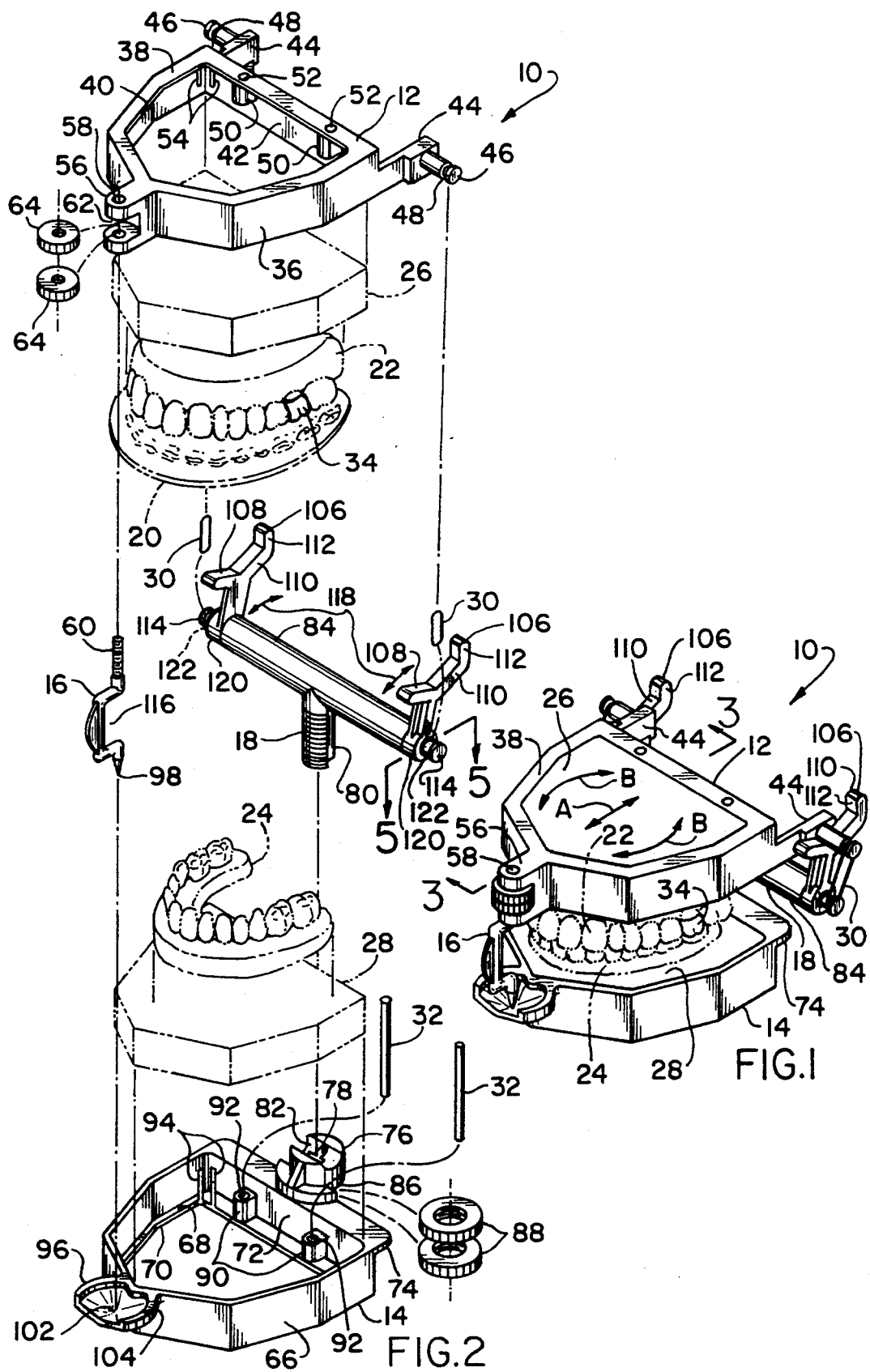

DENTAL ARTICULATOR

The present invention relates generally to improvements in a dental articulator, which is an apparatus in common use for testing the accuracy of dentures during occlusion, and more particularly to improvements which provide all degrees of articulation of the dentures in place in the articulator so that anatomically there is an optimum simulation of the performance of the dentures as would occur in actual use.

In known dental articulators provision is typically limited to making a selected height adjustment of the upper denture relative to the lower denture, and pivotal traverses of the upper denture relative to the stationary lower denture are then used to adjust the "bite" and other use requirements of the dentures. These limited degrees of movement, however, are not all inclusive of the possible movements of the human temporomandibular joint, jawbone, and the like affecting the use requirements of permanent and removable bridges, full upper and/or lower dentures, simple crowns, and other dental appliances.

EXAMPLE OF THE PRIOR ART

In a typical dental articulator, as exemplified by "Dental Articulator" described and illustrated in U.S. Pat. No. 4,417,873 issued to Walenty Kulas on Nov. 29, 1983, height adjustability is contemplated using rods 24, 26 and also pivotal traverses about the axis of hinge pin 40, but the hinge support blocks 32, 34 are fixed in position on the rods 24, 26, thus limiting the degrees of movement of the articulator to two in number, i.e. height and pivotal traverses.

Broadly, it is an object of the present invention to provide a more versatile dental articulator, overcoming the foregoing and other shortcomings of the prior art.

More particularly, it is an object to provide increased degrees of movement in a dental articulator, including the correct height adjustment and pivotal traversing movements, and now also a translation movement in a horizontal plane of the upper positioned denture relative to the stationary lower denture, to thereby contribute to enhancing the testing of the accuracy of dental appliances during occlusion.

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a perspective view of the within inventive dental articulator in a fully assembled condition preparatory to the testing of the osculation of upper jaw and lower jaw dentures;

FIG. 2 is similarly a perspective view, but showing the dental articulator in exploded perspective to better illustrate the manner in which the components thereof are assembled to each other;

Figure 3:
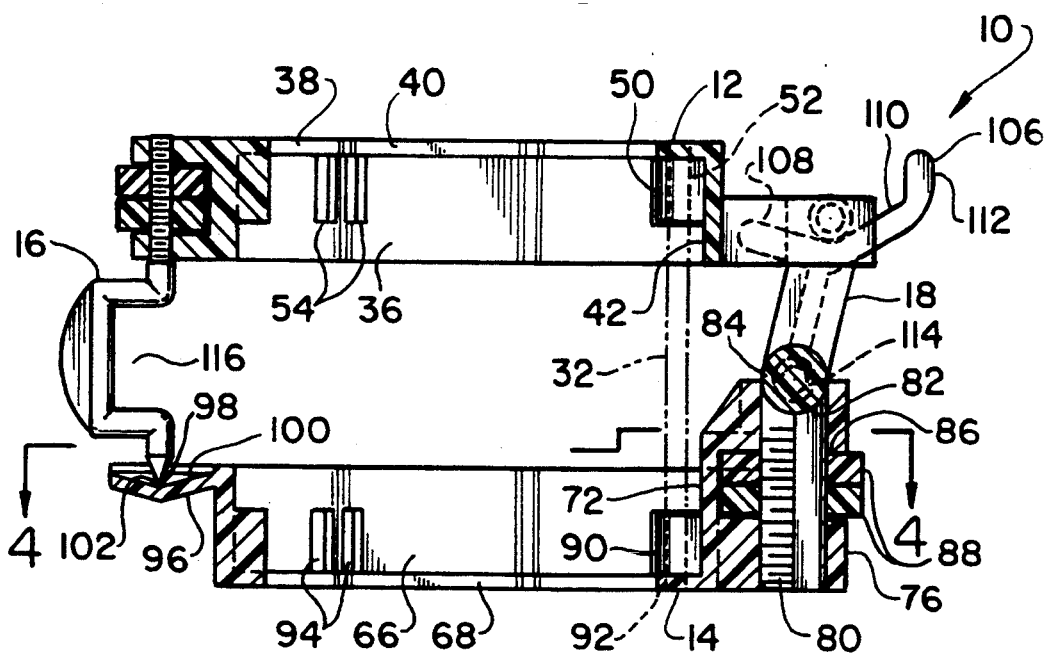
FIG. 3 is a side elevational view in cross section taken along line 3—3 of FIG. 1.
Figure 4:
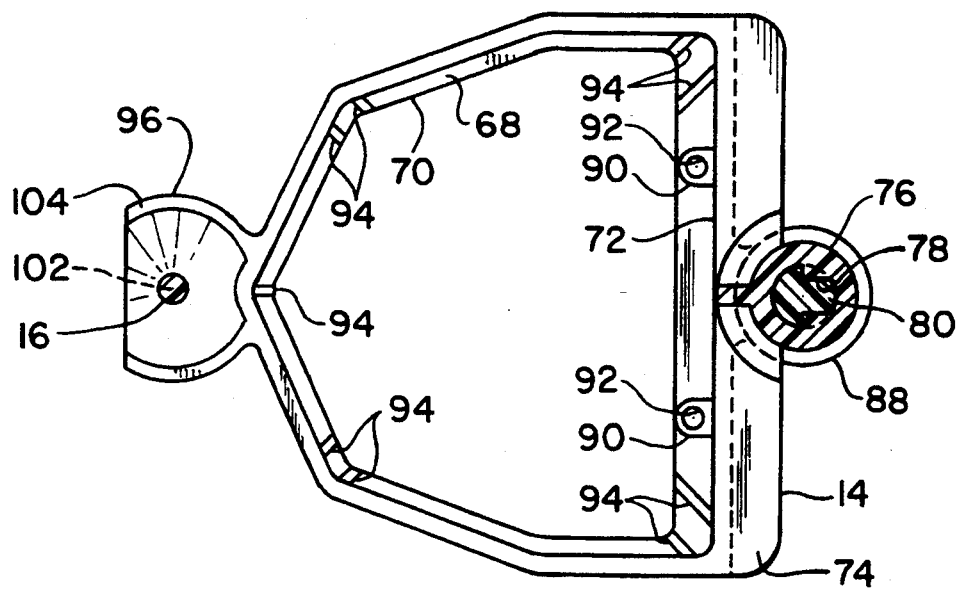
FIG. 4 is a plan view in cross section taken along line 4—4 of FIG. 3.

The within dental articulator, generally designated 10, is preferably of plastic construction material, in which articulating components are intended to simulate anatomically the temporomandibular joint, jawbone and the like, as to the manner in which they functionally cooperate with each other, all to the end of enabling the molder of the dentures to develop an effectively working and fitting dental prosthesis, which typically might be simple crowns, permanent and removable bridges, and even full upper and/or lower dentures which, in dental parlance, are referred to as appliances. Stated somewhat otherwise, it might be intended to provide the patient with upper and lower dentures, and it is tedious to make necessary refinements in the so-called "bite" and other attributes of these dentures by trial and error positionings thereof directly within the patient's mouth. Rather, the alternative conventional practice is to use a dental articulator, of which articulator 10 is exemplary in its function, but not in its construction or operating mode, in which the components of the articulator provide a good simulation of the environment in which the dentures are required to function. Thus, the trial and error positionings are in the articulator 10 and refinements to the dentures are made based thereon, thereby obviating the need to subject the patient to the discomfort and tedium of direct participation in the denture-refining process.

For the purposes intended, articulator 10 consists of an upper frame 12 for receiving in projected relation therein an upper plaster-of-paris cast denture (i.e. maxillary denture), a lower frame 14 for the similarly cast lower denture (i.e. mandibular denture), a frame aligning means 16 the functioning of which will soon be explained, and a rear height-adjusting means 18.

According to conventional practice, in anticipation of the use of the articulator 10, the dentist provides upper and lower dental molds (not shown) and a wax bite registration plate 20 of the patient involved to the dental technician. The technician then makes respective upper and lower castings 22, 24 from the provided molds. After proper trimming, dental castings 22, 24 are appropriately held in relative position about the bite registration impression 20, during which they are positioned within respective frames 12, 14 and held in the frames and in their "bite registration" relation by plaster mix 26, 28. The upper and lower dental casts 22, 24 are maintained in fixed, parallel, spaced and aligned relation by the front and rear aligning means 16, 18, rubber bands 30, and a pair of alignment pins 32, all in accordance with well understood conventional dental articulator practice. When the denture-holding plaster mix 26, 28 has hardened, pins 32 and bite registration plate 20 are removed, and the technician can then proceed to develop any refinement of dental appliance 34 (shown herein as a so-called crown) that may be required for the patient. Such an appliance 34 may typically include, as already noted, such devices as simple crowns, permanent and removable bridges, and full upper and/or lower dentures.

Upper frame 12 has a shaped wall 36 with a flange 38 overhang which bounds an opening 40 for the upper cast denture 22. At the outboard opposite ends of the rear wall 42 of frame 12 a pair of extensions 44 are provided to support a pair of arms 46, each having a groove 48 adjacent its distal end. Internally of wall 42 are a pair of bosses 50 with pin holes 52. An array of ribs 54 on the interior of wall 36 facilitates, according to the so-called DVA system, the positioning in the frame of standard-sized cast dental molds. On the foremost point of frame 12, a protruding extension 56 is provided with a through hole 58 to receive an upper threaded length section 60 of the previously referred-to front aligning pointer 16. Extension 56 also has a horizontal slot 62 to receive a pair of knurled nuts 64 which threadably engage section 60 during the articular set-up or assembly.

The lower or base frame 14 is similar to frame 12 and has a similar multi-sided shaped wall 66 with an inwardly projecting or overhanging flange 68 bounding an opening 70. The rear wall 72 has a rearwardly extending lip 74. A cylindrically shaped extension 76 supported on lip 74 is provided with a T-shaped opening 78 to receive a matching shaped depending extension 80 on an articulator rear suspension member 18. Cylindrical extension 76 has a concave seat 82 for a first pivot construction having as a component a cross bar 84 connected transversely of suspension member 18 and a rearward facing horizontal slot 86 to receive a pair of knurled nuts 88. As in frame 12, frame 14 has a pair of bosses 90 each surrounding a through hole 92 to accommodate alignment pins 32. Also like frame 12, frame 14 has an array of internal support ribs 94 to accommodate a wide range of dental mold cast systems. On the forwardmost point of frame 14 a dish shaped extension 96 serves as a support for the pointed tip 98 on pointer 16. The contoured inside surface 100 of dish 96 has a low point 102 coincident with the vertical center line of pointer 26 and with through hole 58 on frame 12. From this low point 102, surface 100 is circumferentially angularly inclined towards a lip 104.

Returning to the description of rear suspension means 18, it consists of the previously noted first pivot provided by the cross bar 84 and dependent extension 80, and also a third pivot construction comprised in part of a pair of upwardly extending Y-shaped members 106, the second pivot construction being embodied in the construction of upper frame 12 and subsequently to be described. Each of members 106 has respective front and back legs 108,110 and a short vertical leg 112. Members 106 serve as a seat for arms 46 on frame 12 at assembly. Provided on the outboard ends of crossbar 84 are nail-head-like extensions 114 which are used to hold one end of closed loop rubber bands 30, the opposite ends of which are looped about cooperating grooves 48 in arms 46 to thereby provide an urgency holding the frames 12 and 14 in assembled relation.

The construction on upper frame 12 consisting of extensions 44 and the laterally extending cylindrically shaped arms 46 supported thereon provide a pivot axis in the alignment of the arms with each other which, for the articulator 10, function as a second Divot construction.

Thus, and as is perhaps best understood from FIG. 1, pivotal movement of upper frame 12 relative to lower frame 14 is achieved by the degree of pivotal traversing movement of first pivot 18 associated with the lower frame 14 and second pivot 44 associated with the upper frame 12 under the holding bias of rubber bands 30. The third pivot 106 is a still further advantageous adjustment available to the technician to factor into the articulation of frame 12 relative to frame 14, to the end of simulating the natural articulation of the upper and lower jaws of the patient for whom the dental prosthesis is intended. It is to be noted that, although the patient's lower jaw opens and closes relative to his/her upper jaw, the simulation is nevertheless valid in the articulator 10 even though it is the upper frame 12 which "opens and closes" relative to the lower frame 14.

Figure 5:
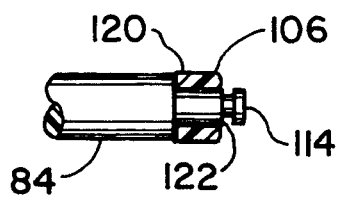
FIG. 5 is a partial cross sectional view as taken along line 5—5 of FIG. 2.

The third pivot function is achieved by molding arms 106 with a through cap (120 (FIG. 5) sized to frictionally engage the stepped down cylindrical opposite ends 122 of the cross bar 84, so that any selected angular orientation can be correspondingly arranged between the members 106 and the longitudinal axis of cross piece 84. In addition to affecting articulation of the frames 12 and 14, the selected angular orientation of the pivots 106 also results in a translation movement denoted by the arrow A (see FIG. 1) of the frame 12 relative to frame 14, and is thus another degree of relative movement which contributes to enabling the technician to develop a proper dental prosthesis.

At assembly, the first pivot depending leg 80 is projected within hole 78 and held by nuts 88 to provide a selected height to the cross bar 84. Likewise at assembly, the upper length portion 60 on pointer 16 is projected within hole 58 and held in place by nuts 64. Nuts 64 and 88 are subsequently rotatively adjusted to modify, as required, the vertical relation between the frames 12 and 14. After adjustment, the pairs of nuts 64 and 88 are jammed together to lock or hold in place the front and rear aligning means 16 and 18. Pointer 16 is preferably provided with an offset 116 which can be swung left or right to avoid blocking the observation of the middle alignment of the upper and lower anterior central or lateral teeth on the dentures or models 22 and 24.

During the development of a prosthesis 34, the technician can move the upper frame 12 relative to the lower frame 14 in a back and forth or translation degree of movement A, and arcuate side to side degree of movement B, as noted in FIG. 1, as well as, of course, in pivotally traversing movement. Thus, the construction and operating mode of the within articulator 10 effectively simulates the natural jaw movements that take place and affect the interaction of upper and lower teeth during chewing, biting, grinding and speech, and thus is a significant aid to the technician in developing the physical structural aspects and features of the prosthesis to enable it to serve its purpose when in actual use.

While the dental articulator herein shown and disclosed in detail is fully capable of attaining the objects and providing the advantages hereinbefore stated, it is to be understood that it is merely illustrative of the presently preferred embodiment of the invention, and that no limitations are intended to the detail of construction or design herein shown other than as defined in the appended claims.

What is claimed is:

1. A dental articulator of a type having a pivotal mounting for a denture in a dental cast upper jaw and for a denture in a dental cast lower jaw preparatory to testing the accuracy of said dentures during occlusion thereof, the improvements in said pivotal mounting comprising a first horizontally oriented pivot member disposed rearwardly of said dental cast lower jaw having opposite ends serving as male connection means, a second horizontally oriented pivot member disposed rearwardly of said dental cast upper jaw having opposite ends serving as pivot axle means for said dental cast upper jaw, a pair of third pivot members each having at opposite ends a female connection means and an arcuate support for said pivot axle means of said dental cast upper jaw, each said third pivot member having an operative position in angular relation to said dental cast lower jaw first pivot member determined by a corresponding rotative position of said cooperating female and male connection means for positioning said denture of said dental cast upper jaw in a horizontal plane relative to said denture of said dental cast lower jaw after which said dental cast upper jaw is provided with an operative position in which said pivot axle means of said dental cast upper jaw is disposed in a pivotal relation in a said cooperating arcuate support of said third pivot member, and a pair of closed loop rubber bands each disposed in encircling relation about one said axle means of said dental cast upper jaw and female connection means of said third pivot member, whereby said dental cast upper jaw can be urged through pivotal traverses relative to said dental cast lower jaw to test the accuracy during occlusion of said dentures thereof.

2. The dental articulator as claimed in claim 1 wherein said dental cast lower jaw has an upstanding hub with a central opening therein and said first pivot member has a depending pin sized to be projected into said central opening, whereby said first pivot member is adjustable in its vertical position relative to said dental cast lower jaw to allow corresponding adjustment in the vertical position of said dental cast upper jaw relative to said dental cast lower jaw.

3. The dental articulator as claimed in claim 2 wherein each said third pivot member female connection means has an outwardly laterally extending pin to facilitate the encirclement thereof by a cooperating one said rubber band.

* * * * *